United States Patent [19]

Bolin

[11] Patent Number: 4,822,890

[45] Date of Patent: Apr. 18, 1989

[54] METHOD FOR THE PRODUCTION OF AMINO TERMINUS PROTECTED NATURALLY OCCURRING AMINO ACIDS

[75] Inventor: David R. Bolin, Denville, N.J.

[73] Assignee: Hoffmann-La Roche Inc., Nutley, N.J.

[21] Appl. No.: 877,826

[22] Filed: Jun. 24, 1986

Related U.S. Application Data

[63] Continuation of Ser. No. 772,238, Jun. 11, 1985, abandoned, which is a continuation-in-part of Ser. No. 496,775, May 20, 1983, abandoned.

[51] Int. Cl.$^4$ ............... C07D 209/20; C07D 233/18; C07C 99/00
[52] U.S. Cl. ..................... 548/344; 548/496; 548/497; 548/532; 562/445; 562/562; 562/563; 562/570; 562/554
[58] Field of Search ............... 548/497, 496, 532, 344; 562/554, 562, 563, 570, 445

[56] References Cited

U.S. PATENT DOCUMENTS

| | | | |
|---|---|---|---|
| 3,529,006 | 9/1970 | Senge et al. | 556/419 |
| 3,835,175 | 9/1974 | Carpino et al. | |
| 3,839,396 | 10/1974 | Otsuka et al. | |
| 3,856,848 | 12/1974 | Smithwick. | |
| 3,906,031 | 9/1976 | Carpino et al. | |
| 4,608,270 | 8/1986 | Varapratm | 556/419 |

OTHER PUBLICATIONS

Smithwick et al. "A New Synthesis of $N^a, N^G, N^G$-Tribenzyloxycarbonyl-L-Arginine and Related Derivatives", J. Org. Chem., 1974 39 3441–3442.

Barlos et al, "Efficient 'One-Pot' Synthesis of N-Trityl Amino Acids", J. Org. Chem., 1982, 47:1324–1326.

Bodansky, Y. Klausner and Mr. Ondetti "Peptide Synthesis", 2nd Ed., "Protection of Amino Acids", pp. 43 and 44.

Chang et al. "Preparation and Properties of $N\alpha$-9-Fluoroenylmethyloxy Carbonylamino Acids Bearing Protein Tert.-Butyl Side Chain Protection"–Int. J. Peptide Prot. Res. 1980 15 59–66.

Merrifield et al. "9-(2-Sulfo)fluorenylmethyloxycarbonyl Chloride, A New Reagent for the Purification of a Synthetic Peptide", J. Org. Chem. 1978, 43:4808–4816.

Carpino et al. "The 9-Fluorenylmethoxycarbonyl Amino Protecting Group", J. Org. Chem. 1972, 37:3404–3409.

Theodropolos et al. J. Org. Chem., 47 p. 1324 et seq. (1982).

*Primary Examiner*—David B. Springer
*Attorney, Agent, or Firm*—Jon S. Saxe; George M. Gould; Julie M. Prlina

[57] ABSTRACT

A method for the production of substantially 100% pure $N\alpha$-urethane protected amino acids is disclosed. This method eliminates the formation of di-peptide and tri-peptide contaminants. Reaction of blocking reagents at the carboxylate site on a protected peptide is prevented by the application of labile amino acid esters. Subsequent removal of the ester yields, in ultra-high purity, the $N\alpha$-protected amino acid. The substantially 100% pure $N\alpha$-urethane protected amino acid are also disclosed.

9 Claims, No Drawings

METHOD FOR THE PRODUCTION OF AMINO TERMINUS PROTECTED NATURALLY OCCURRING AMINO ACIDS

RELATED APPLICATIONS

This is a continuation of application Ser. No. 772,238 filed June 11, 1985, abandoned, which is a continuation-in-part of Ser. No. 496,775, filed May 20, 1983, abandoned.

FIELD OF THE INVENTION

This invention relates to Nα-urethane protected amino acids and a method for their production.

BACKGROUND OF THE INVENTION

It has been observed that many preparations of Nα-urethane protected amino acids are contaminated with significant amounts of di- and tripeptides. In the reactions used by the prior art to synthesize these protected amino acids, the protecting group acylating reagent, 1, $$ROCCl \quad \underline{1}$$

is reacted with an amino acid, 2, $$NH_2CHCO_2H \text{ (with } R^1\text{)} \quad \underline{2}$$

to form a Nα protected amino acid, 3, $$ROCNHCHCO_2H \text{ (with } R_1\text{)} \quad \underline{3}$$
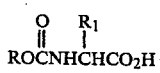

and HCl.

where R is alkyl or arylalkyl and R' represents the amino acid side chain. In most circumstances, these reactions are run in aqueous/organic solvents with an inorganic base (such as sodium carbonate, magnesium oxide, etc.) to neutralize the HCl formed. The conditions, termed Schotten-Baumann, leave the carboxyl group exposed as a carboxylate anion coordinated with a metal cation, 4, $$ROCNHCHCO_2^- \, M^+ \text{ (with } R'\text{)} \quad \underline{4}$$

which can undergo reaction with a second molecule of reagent 1 to form a reactive species called a mixed anhydride, 5, $$ROCNHCHCOCOR \text{ (with } R'\text{)} \quad \underline{5}$$

This intermediate can react with a second amino acid molecule 2 to form the Nα-blocked dipeptide, 6.

$$ROCNHCHCNHCHCO_2^- \, M^+ \quad \underline{6}$$

This process can repeat to produce decreasingly smaller amounts of higher homologues (tripeptides, tetrapeptides, etc.).

The amounts of contaminating peptide impurities are dependent on a variety of factors including type of acylating agent, base, solvent, temperature, and pH. Research has been performed in order to optimize these parameters, however, all conditions found by the prior art lower but do not eliminate the impurities.

To prevent this reaction, the carboxyl group must be blocked, preferably as a labile ester. Trimethylsilyl (Tms) esters are known to be readily formed and easily hydrolyzed back to the carboxylic acid. Smithwick and Shuman [2] relied on transient trimethylsilyl protection to prepare $N^\alpha,N^G,N^G$-tribenzyloxycarbonyl-L-arginine, which could previously only be formed in low yields by known routes. However, Smithwick and Shuman utilized a multistep procedure which required both the formation of lithium salts and resulted in a low yield of the final product. Theodoropoulos and co-workers, J. Org. Chem. 47, 1324 (1982), utilized Tms in the syntheses of Nα-trityl amino acids. The trityl group, however, is greatly different in reactivity and size from most blocking groups. In addition, due to the chemistry of the trityl groups formation of peptide contaminants is probably not a problem. In addition the use of the Tms group in this reference is different from the present invention in that the amino group of the particular amino acid is not silylated when the desired blocking roup is attached to the amino acid (the intermediate being silylated at positions other than the Nα-amino group) and this reference utilizes methanol solvolysis as opposed to aqueous hydrolysis. Presumably, the high yields obtained by this procedure were the result of the facile methanol solvolysis of the Tms ester at the end of this particular synthetic route.

The prior art, however, did not recognize that contaminating peptide formation could be entirely prevented during the synthesis of Nα-blocked amino acids regardless of the particular blocking group used during the synthesis procedure or that the synthesis procedure could utilize aqueous base hydrolysis conditions. It is, therefore, an object of this invention to eliminate the formation of these contaminants when producing Nα-blocked amino acids.

SUMMARY OF THE INVENTION

The method of this invention effectively prohibits formation of peptide contaminants during the formation of Nα-blocked amino acids. Reaction of blocking reagents at the carboxylate site is prevented by the application of labile amino acid esters. Subsequent removal of the ester yields the Nα-protected (or amino-terminus protected) amino acid. The FMOC derivatives of all the common amino acids have been synthesized by this method, in yields generally >95%, and with no detectable peptide impurities. The method is clean, rapid, and applicable to a variety of side chain protecting functions. Additionally, this method has been utilized with several other urethane blocking groups, such as Z, TrOC, and BOC, with similarly excellent results.

DETAILED DESCRIPTION OF THE INVENTION

It has been recently recognized that the synthesis of $N^\alpha$-blocked amino acids is accompanied by the formation of peptide bonds. The resultant di- and tripeptides contaminate the desired monomeric product and create substantial difficulties during subsequent purification. These impurities can occur to the extent of 2-5% or more and can cause serious problems during the synthesis of medium or large peptides. It would be extremely desirable to eliminate these impurities at the initial synthetic stages rather than rely on costly purification steps.

Most commercially available 9-fluorenylmethyloxycarbonyl (Fmoc) amino acids have been found to be severely contaminated with peptide impurities. An examination of several substances by amino acid analysis was performed and the data are shown in Table I. Although tripeptides only occurred in trace amounts, the dipeptide contents were high enough to be bothersome during subsequent peptide synthesis.

By analysis of the mechanism of impurity formation and a survey of the literature, a promising and previously unknown solution to the contamination problem was surprisingly discovered. Theodoropoulos and coworkers [1] had utilized the trimethylsilyl esters of amino acids to synthesize the $N^\alpha$-trityl derivative of amino acids. However, application of this background to the formation of Fmoc and other protected amino acids was intriguing because this had never been done with blocking groups other than trityl while also utilizing aqueous base hydrolysis conditions specifically to prevent the contamination problem and because use of the trimethylsilyl esters would eliminate totally the possibility of reaction at the carboxyl group and prevent dipeptide contamination.

Novel procedures were developed along these lines and excellent results were obtained by this inventive method. Table II lists several of the protected amino acids which have been prepared to date. High yields (~95%) have been realized on batches in the 7-8 gram range. Of prime importance was the fact that di- and tripeptide contamination was nonexistent. The blocked amino acids so afforded were of high purity and could be employed in further synthetic operations without additional purification.

A comparison of the purity of materials formed by this method to that from other sources illustrates the superiority of the present invention. The advantages of the claimed invention are: (1) a "one-pot" process, (2) easy isolation of products, (3) rapid reactions with high yields, (4) cost competitive with normal routes, (5) high purity final products, (6) an aqueous base hydrolysis may be used and (7) it does not result in the formation of intermediate salts which require separate isolation steps.

Additional examples set forth herein demonstrate that this method is applicable to synthesis of carbobenzoxy amino acids, and other protecting groups, with equally excellent results. Yields are high and peptide contamination is eliminated.

TABLE I

Peptide Contaminants in Fmoc—AA

|  | AA | AA—AA | AA—AA—AA |
|---|---|---|---|
| Fmoc—Gly—OH |  |  |  |
| R-3385 Bachem | 85.4 | 14.4 | 0.2 |
| 7967-45 Chang | 97.7 | 2.3 | <0.18 |
| PL-70-35A Goodman | 99.3 | 0.7 | <0.15 |
| Fmoc—Ala—OH |  |  |  |
| 8615-300B Chang | 95.8 | 4.2 | <0.11 |
| 8615-300A Chem. Dyn. | 99.0 | 1.0 | <0.11 |
| Fmoc—Leu—OH 105236 Chem. Dyn. | 98.01 | 1.99 | B.D.L.* |
| Fmoc—Ile—OH 7967-156-15 | 100.00 | B.D.L. | B.D.L.* |
| Fmoc—Glu(OtBu)—OH |  |  |  |
| 8615-299A Chang | 94.9 | 5.1 | N.D.** |
| 106-101 Galactica | 95.5 | 4.5 | N.D.** |
| Fmoc—Lys(Boc)—OH 10556-13A-1 | 98.4 | 1.6 | N.D.** |
| Fmoc—Ser(tBu)—OH 105771 Chem. Dyn. | 98.40 | 1.60 | B.D.L.* |

*Below Detection Level
**Not Determined

TABLE II

|  | Crude Yield | Recryst. Yield | Purity[a] | mp[b] | $[\alpha]25^{b,c}$ D |
|---|---|---|---|---|---|
| Fmoc—Gly | 97.6% | 88% | 100% | 173-5° (173-4°) | −18.62 (−18.6) |
| Fmoc—Ala | 99.4 | 89 | 100 | 141-2° (143-4°) | −38.71 (−37.6) |
| Fmoc—Phe | 97 | 82 | 100 | 183-4° (181-3°) | −38.71 (−37.6) |
| Fmoc—Val | 94.1 | 88 | 100 | 145-6° (143-5°) | −16.97 (−16.1) |
| Fmoc—Pro | 96 | 94 | 100 | 96-9° (114-5°) | −33.34 (−33.9) |
| Fmoc—Gln | 100 | 82 | 100 | 223-4° (221-3°) | −18.10 (−17.0) |
| Fmoc—Met | 93 | 78 | 100 | 133-4° (129-132°) | −29.24 (−28.3) |
| Fmoc—Trp | 98.5 | 93 | 100 | 182-3° (165-6°) | −27.76 (−26.6) |
| Fmoc—Asp(OtBu) | 91.8 | 87 | 100 | 149-152 (148-9°) | −22.54 (−20.3) |
| Fmoc—Leu | 92.3 | 86 | 100 | 153-4° (153-4°) | −25.33 (−24.1) |
| Fmoc—Ile | 94.4 | 88 | 100 | 148-9° (145-7°) | −12.44 (−11.9) |
| Fmoc—Glu(OtBu) | 94 | 86 | 100 | 82-4° (76-7°) | +1.27 (+0.8)[d] |
| Fmoc—Lys(Boc) | 91 | 84 | 100 | 132-4° (123-4°) | −11.93 (−11.7) |
| Fmoc—Ser(tBu) | 100 | 93 | 100 | 128-131° (126-9°) | +26.08 (+25.4)[d] |
| Fmoc—Asn | 99 | 89 | e | 187-8° (185-6°) | −11.85 (−11.4) |
| Fmoc—Cys(StBu) | 97.3 | 65 | e | 75-8° (74-6°) | −82.88 (−84.6)[d] |
| Fmoc—Thr(tBu) | 100 | 89 | e | 133-4° (129-132°) | −5.47 (−4.5) |
| Fmoc—Tyr(tBu) | 90 | 85 | 100 | 150-1° (150-1°) | −27.34 (−27.6) |

[a]Determined by ion exchange chromatography on a Beckman 121M Amino Acid Analyzer.
[b]Literature values 3 in parentheses.
[c]In dimethylformamide (c = 1) except where indicated.
[d]In ethyl acetate.
[e]Not determined by amino acid analysis.
Oligomeric standards not available.
Homogeneous by TLC.

Abbreviations used throughout this specification are as follows:

| Abbreviations: | |
|---|---|
| Tms | Trimethylsilyl(CH₃)₃Si— |
| Tms—Cl | Trimethylsilylchloride(CH₃)₃SiCl |
| Fmoc | 9-Fluorenylmethyloxycarbonyl |
| DIPEA | Diisopropylethylamine[(CH₃)₂CH]₂NCH₂CH₃ |
| Boc | t-Butyloxycarbonyl |
| Z | Benzyloxycarbonyl |

This invention generally comprises a method for the synthesis of Nα-urethane protected amino acids, such as 9-Fluoroenylmethyloxycarbonyl (Fmoc) amino acids 7. As detailed in the Experimental Section, the desired amino acid is reacted with 2 equivalents

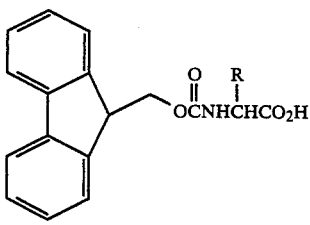

7

(3 equivalents if a reactive side chain function is present) of trimethylsilyl chloride (Tms-Cl) 8 in methylene chloride (Equation III).

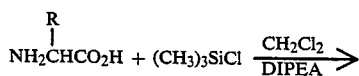

(III)

8

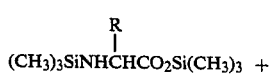

9

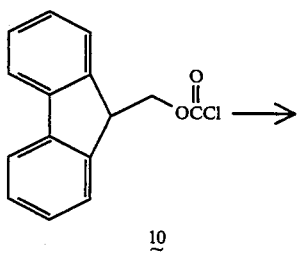

10

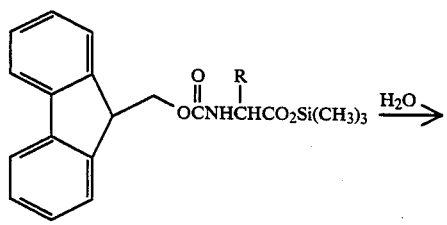

11

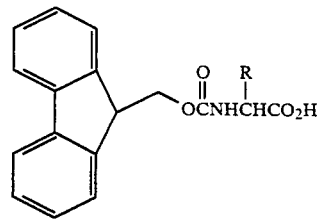

This is preferably followed by an organic base, such as diisopropylethylmaine (DIPEA). It is forseeable that bases such as triethylamine, trimethylamine, N-methylmorpholine or other tertiary amines would be equally applicable. Choice of the base would be dependent on functional group reactivity and stability. The intermediate 9 is then reacted with the Fmoc acylating species 10 to give the Fmoc amino acid Tms ester, which upon hydrolysis, preferably base hydrolysis, gives the Fmoc amino acid 11. As previously stated, yields are high, the reaction is fast, and the product is free of di- and tripeptide contaminants. The reaction can be carried out successfully regardless of whether the base is added prior to, simultaneously with or following the silylating agent. However, depending on the presence of particular side chain protecting groups, such as those on O-t-butyl-serine, Nε-Boc-lysine, etc, it is preferrable that the base be added prior to the silylating agent. It is additionally forseeable in the practice of this invention that other silylating agents may be utilized such as trimethylsilylacetamide, trimethylsilylylimidazole, trimethylsilyldiethylamine, and N,O-bis(trimethylsilyl) acetamide.

Significantly, this invention's method can be applied to other blocking groups of the form

For instance, this procedure can be used for the other groups such as the carbobenzoxy (Z) group. In addition, other Nα-urethane blocking groups such as t-butyloxycarbonyl, and 2,2,2-trichloroethyloxycarbonyl which are known to suffer the same peptide bond formation side reaction as Fmoc, may also be used with the method of this invention without formation of contaminating peptides.

The following examples will further illustrate the method of the invention and the substantially 100% pure Nα-blocked amino acid produced thereby.

EXAMPLE 1

Preparation of Fmoc Derivatives of Phe, Val, Pro, Met, Trp, Leu, Ile, Ala

Fmoc derivatives of the above commercially available amino acids (from Chemical Dynamics Corp. S. Plainfield, N.J.) were each prepared separately according to the following procedure. 37.5 mmoles of finely ground amino acid was placed in a 250 mL round bottom flask (oven dried) which was fitted with a heating mantle and condenser (oven dried). A nitrogen gas line was attached at the top of the condenser. The solid was suspended in 87.5 mL distilled, dry methylene chloride and stirred vigorously. 9.52 mL (75 mmoles) of Tms-Cl (Aldrich Chemical Co., Milwaukee, WI) was injected in one portion. The mixture was refluxed for 1 hour and cooled in an ice bath. 11.3 mL (100 mmoles) of diisopropylethylamine was carefully added. 9-Fluorenylmethyloxycarbonyl chloride (commercially available from Chemical Dynamics Corp.) (6.47 g, 25 mmoles) was added in one portion. The solution was stirred in ice for 20 minutes and warmed to room temperature for 1–1.5 hrs. The mixture was concentrated on a rotary evaporator and then distributed between 200 mL diethyl ether and 250 mL 2.5% sodium bicarbonate. The phases were separated and the aqueous layer was extracted with 2×50 mL diethyl ether. The ether layers were backwashed with 2×25 mL H$_2$O. The combined aqueous layers were acidified to pH 2 with 1.0N HCl and extracted with 3×75 mL ethyl acetate. The organic layers were dried over sodium sulfate, concentrated to an oil and dried by azeotroping with 2×30 mL acetonitrile. The oil solidified by pumping under high vacuum. Appropriate solvents were used to recrystallize the product. Products were found to be homogeneous (Table II).

EXAMPLE 2

Preparation of Fmoc Derivatives of Gly and Cys(StBu)

Fmoc derivatives of the above commercially available amino acids (from Chemical Dynamics Corp.) were each prepared separately according to the following procedure. 31.25 mmoles of finely ground amino acid was placed in a 250 mL round bottom flask (oven dried) which was fitted with a heating mantle and condenser. The solid was suspended in 87.5 mL distilled, dry methylene chloride and stirred vigorously. 7.43 mL (62.5 mmoles) of Tms-Cl was injected in one portion. The mixture was refluxed for 1 hour and cooled in an ice bath. 9-Fluorenylmethyloxycarbonyl chloride (6.47 g, 25 mmole) and 9.89 mL (87.5 mmole) of diisopropylethylamine were added. The solution was stirred in ice for 20 minutes and warmed to room temperature for 1–1.5 hrs. The mixture was concentrated on a rotary evaporator and then distributed between 200 mL diethyl ether and 250 mL 2.5% sodium bicarbonate. The phases were separated and the aqueous layer was extracted with 2×50 mL diethyl ether. The ether layers were backwashed with 2×25 mL H$_2$O. The combined aqueous layers were acidified to pH 2 with 1.0N HCl and extracted with 3×75 mL ethyl acetate. The organic layers were dried over sodium sulfate, concentrated to an oil and dried by azeotroping with 2×30 mL acetonitrile. The oil solidified by pumping under high vacuum. Appropriate solvents were used to recrystallize the product. Products were found to be homogeneous (Table II).

EXAMPLE 3

Preparation of Fmoc Derivatives of Glu(OtBu), Asp(OtBu), Thr(tBu), Ser(tBu), Lys(Boc)

Fmoc derivatives of the above commercially available amino acids (from Chemical Dynamics Corp.) were each prepared separately according to the following procedure. 37.5 mmoles of finely ground amino acid was placed in a 250 mL round bottom flask (oven dried) which was fitted with a heating mantle and condenser (oven dried). A nitrogen gas line was attached at the top of the condenser. The solid was suspended in 87.5 mL distilled, dry methylene chloride and stirred vigorously. Diisopropylethylamine (12.7 mL, 112.5 mmole) was added. 9.52 mL (75 mmole) of Tms Cl was injected carefully. This mixture was refluxed for 1.5 hours and then cooled in an ice bath. 9-Fluorenylmethyloxycarbonyl chloride (6.47 g, 25 mmole) was added in one portion. The solution was stirred in ice for 20 minutes and warmed to room temperature for 1–1.5 hrs. The mixture was concentrated on a rotary evaporator and then distributed between 200 mL diethyl ether and 250 mL 2.5% sodium bicarbonate. The phases were separated and the aqueous layer was extracted with 2×50 mL diethylether. The ether layers were backwashed with 2×25 mL H$_2$O. The combined aqueous layers were acidified to pH 2 with 1.0N HCl and extracted with 3×75 mL ethyl acetate. The organic layers were dried over sodium sulfate, concentrated to an oil and dried by azeotroping with 2×30 mL acetonitrile. The oil solidified by pumping under high vacuum. Appropriate solvents were used to recrystallize the product. Products were found to be homogeneous (Table II).

EXAMPLE 4

Preparation of Fmoc-Asn 4.95 g (37.5 mmoles) of finely ground asparagine (Chemical Dynamics Corp.) was placed in a 250 mL round bottom flask (oven dried) which was fitted with a condenser (oven dried). A nitrogen gas line was attached at the top of the condenser. The solid was suspended in 87.5 mL of dry N,N-dimethylacetamide and stirred vigorously. 19.04 mL (150 mmoles) of Tms-Cl was injected in one portion. The mixture was stirred for 1 hour and cooled in an ice bath. 9-Fluorenylmethyoxycarbonyl chloride (6.47 g, 25 mmoles) and 19.78 mL (175 mmoles) of diisopropylethylamine were added. The solution was stirred in ice for 20 minutes and warmed to room temperature for 1–1.5 hrs. The mixture was concentrated on a rotary evaporator and then distributed between 200 mL diethyl ether and 250 mL 2.5% sodium bicarbonate. The phases were separated and the aqueous layer was extracted with 2×50 mL diethyl ether. The ether layers were backwashed with 2×25 mL H$_2$O. The combined aqueous layers were acidified to pH 2 with 1.0N HCl. The white precipitate was filtered and washed with cold H$_2$O. The product was then dried overnight. Appropriate solvents were used to recrystallize the product. The product was found to be homogeneous (Table II).

EXAMPLE 5

Preparation of Fmoc-Gln 5.48 g (37.5 mmoles) of finely ground glutamine (Chemical Dynamics Corp.) was placed in a 250 mL round bottom flask (oven dried) which was fitted with a heating mantle and condenser (oven dried). A nitrogen gas line was attached at the top of the condenser. The solid was suspended in 87.5 mL of dry N,N-dimethyl-acetamide and stirred vigorously. 19.04 mL (150 mmoles) of Tms-Cl was injected in one portion. The mixture was warmed slightly for 1 hour and cooled in an ice bath. 9-Fluorenylmethyloxycarbonyl chloride (6.47 g, 25 mmoles) and 19.78 mL (175 mmoles) of diisopropylethylamine were added. The solution was stirred in ice for 20 minutes and warmed to room temperature for 1–1.5 hrs. The mixture was concentrated on a rotary evaporator and then distributed between 200 mL diethyl ether and 250 mL 2.5% sodium bicarbonate. The phases were separated and the aqueous layer was extracted with 2×50 mL diethyl ether. The ether layers were backwashed with 2×25 mL H$_2$O. The combined aqueous layers were acidified to pH 2 with 1.0N HCl.

The white precipitate was filtered, washed with cold H₂O and dried under high vacuum. Appropriate solvents were used to recrystallize the product. The product was found to be homogeneous (Table II).

EXAMPLE 6

Preparation of Fmoc-Tyr(tBu)

6.52 g (27.5 mmoles) of finely ground O-t-butyl-tyrosine (Chemical Dynamics Corp.) was placed in a 500 mL round bottom flask (oven dried) which was fitted with a condenser (oven dried). A nitrogen gas line was attached at the top of the condenser. The solid was suspended in 100 mL of dry dioxane and stirred vigorously. Diisopropylethylamine (9.04 mL, 80 mmoles) was added. Tms-Cl (6.98 mL, 55 mmoles) was added and let stir for 1 hour. Methylene chloride (200 mL) was added and the entire mixture was chilled in an ice bath. 9-Fluorenyl-methyloxycarbonyl chloride (6.47 g, 25 mmole) was added in one portion. The solution was stirred in ice for 20 minutes and warmed to room temperature for 1-1.5 hrs. The mixture was concentrated on a rotary evaporator and then distributed between 200 mL diethyl ether and 250 mL 2.5% sodium bicarbonate. The phases were separated and the aqueous layer was extracted with 2×50 mL diethyl ether. The ether layers were backwashed with 2×25 mL H₂O. The combined aqueous layers were acidified to pH with 10% citric acid and extracted with 600 mL methylene chloride. The organic layers were dried over sodium sulfate, concentrated to an oil and dried by azeotroping with 2×30 mL acetonitrile. The oil solidified by pumping under high vacuum. Appropriate solvents were used to recrystallize the product. The product was found to be homogeneous (Table II).

EXAMPLE 7

Tert-Butyloxycarbonyl-L-Alanine (Also Known As t-Boc Ala)

L-Alanine (Chemical Dynamics Corp.) (2.67 g, 30 mmoles) was suspended in 87.5 mL methylene chloride. Trimethylsilylchloride (10.78 mL, 85 mmoles) was added and refluxed for 1.5 hours. The mixture was cooled to 0° C. Diisopropylethyl amine (11.3 mL, 100 mmoles) was added, followed by Ditert-butyl-dicarbonate (commercially available from FLUKA Chemical Corp. Hauppauge, N.Y.) (5.46 g, 25 mmoles). The mixture was stirred for 20 minutes then warmed to room temperature for 2 hours. The solvent was evaporated and the residue was distributed between 50 mL 2.5% sodium bicarbonate and 50 mL diethyl ether. The aqueous layer was separated, washed with 2×30 mL ether, and acidified to pH 2 with citric acid solution. This mixture was saturated with sodium chloride and extracted with 3×40 mL methylene chloride. The combined organic layers were washed carefully with 2×1 mL H₂O and dried. Concentration yielded 3.6 g (76%) of a white solid.

Amino acid analysis showed no Ala-Ala or Ala-Ala-Ala present.

EXAMPLE 8

N-Carbobenzoxy-L-Thiazolidine-4-Carboxylic Acid (Also Known As Z-Thi)

3.33 g (25.0) mmoles) of L-Thiazolidine-4-carboxylic acid (Chemical Dynamics Corp.) was suspended in 75 mL of dry methylene chloride. 6.35 mL (50.0 mmoles) of trimethylsilylchloride was injected. The mixture was refluxed for 1 hour with vigorous stirring. The reaction was then cooled to 0° C. in an ice bath and diisopropylethylamine (11.0 mL, 97.2 mmoles) was added slowly. Once addition was complete, 5.50 g (32.2 mmoles) of carbobenzoxychloride (commercially available from Chemical Dynamics Corp) was added. The mixture was stirred at 0° for 30 minutes then at room temperature for 1.5 hours. The solvent was evaporated and the residual oily solid partitioned between 100 mL 2.5% sodium bicarbonate and 50 mL of diethyl ether. The aqueous layer was separated, extracted with 2×30 mL ether and acidified to pH with 1.0N HCl. Extraction with 3×50 mL ethyl acetate, followed by drying and concentration yielded 6.0 g (90%) of a clear oil.

HPLC: Homogeneous; $[\alpha]_D - 92.61°$ (C=0.9, MeOH).

Anal. Cald. for $C_{12}H_{13}NO_4S$(267.26): C, 53.92; H, 4.90; N, 5.24; S, 11.99. Found: C, 53.72; H, 5.06; N, 5.41; S, 11.72.

EXAMPLE 9

2,2,2-Trichloroethyloxycarbonyl-L-Phenylalanine (Also Known as TrOC-Phe)

4.96 g (30 mmoles) of L-phenylalanine and 7.61 mL (60 mmoles) of trimethylsilylchloride in 87.5 mL methylene chloride were refluxed for 1.5 hours. The mixture was cooled to 0° C. 5.30 g (25 mmoles) of trichloroethyl chloroformate (commercially available from Chemical Dynamics Corp.) and 9.61 mL (85 mmoles) diisopropylethylamine were added. Stirring was continued for 20 minutes at 0° C. then for 2 hours at room temperature. The solvent was evaporated and the residue dissolved in 2.5% sodium bicarbonate. The aqueous mixture was extracted twice with diethyl ether, acidified to pH 4 with 1N HCl, and extracted three times with ethyl acetate. The combined ethyl acetate layers were dried and concentrated to yield 8.1 g (95%) of a white solid. Recrystallization from ether/petroleum ether yielded small needles, mp 129.5°-131° C. $[\alpha]_D - 1.74°$ (C=0.97, MeOH).

Amino acid analysis showed no Phe-Phe or Phe-Phe-Phe present.

Anal. Cald. for $C_{12}H_{12}C_3NO_4$(340.55): C, 42.32; H, 3.55; N, 4.11, Cl, 31.23. Found: C, 42.20; H, 3.49; N, 4.18; Cl, 31.42.

EXAMPLE 10

Synthesis of Z-Aspartic Acid

Aspartic acid (100 g, 0.75 mol) was suspended in 400 ml methylene chloride and stirred mechanically. Trimethylsilyl chloride (244 g, 2.25 mol) was added. The mixture was refluxed for 1.5 hours and then cooled in an ice bath. Triethylamine (303 g, 3.0 mol) was slowly added with stirring and cooling. Carbobenzoxy chloride (128 g, 0.75 mol) was slowly added with cooling. The mixture was stirred for 2 hours at 0° C. and then warmed to RT for 2 hours. The reaction mixture was poured into a stirred mixture of 500 ml 2.5% NaHCO₃ and 500 ml Et₂O. The layers were separated and the aqueous phase was extracted with 3×300 ml Et2O. The aqueous layer was acidified to pH 2 with conc. HCl and extracted with 3×200 ml EtOAc. The combined organic layers were dried over MgSO₄, filtered and concentrated to a white solid. Recrystallization from 290 ml H₂O yielded 145 g (72.3%) Z-aspartic acid.

EXAMPLE 11

Synthesis of Z-3-Methyl-Histidine

3-Methyl-histidine (commercially available from Sigma Chemical Co., St. Louis, Mo.) (483 mg, 2.58 mmol) was suspended in 50 ml methylene chloride and to this was added 1.26 g (11.6 mmol) of trimethylsilyl chloride. The mixture was stirred and refluxed for 1 hour and then cooled in an ice bath. Diisopropylethylamine (2.0 g, 15.5 mmol) was slowly added. Carbobenzoxy chloride (662 mg, 3.88 mmol) was added and the entire mixture was stirred at RT for 4 hours. The methylene chloride was evaporated and 30 ml $H_2O$ was added. The solution was extracted with $3\times 5$ ml Et20 and this aqueous layer was acidified to pH 2.5 with conc. HCl. This solution was lyophilized to give a white powder. This material was purified on a Magnum 20-ODS3 reversed phase column with a linear gradient of 0–20% CH3CN—$H_2O$. The main peak was collected and lyophilized to yield a white, amorphous powder (650 mg, 83%) of Z-3-methyl-histidine.

HPLC: Homogeneous; mp 191°–194° C.; 100 MHz NMR (DMSO-$d_6$): 2.86 (dd, 1H), 3.03 (dd, 1H), 3.54 (S, 3H), 4.22 (m, 1H), 5.00 (S, 2H), 6.70 (S, 1H), 7.32 (m, 5H), 7.55 (S, 1H), 7.64 (d, J=6 Hz, 1H).

Anal. Cald. for $C_{15}H_{17}N_3O_4 \cdot \frac{1}{2}H_2O$ (312.32): C, 57.69; H, 5.81; N, 13.46. Found: C, 57.82; H, 5.90; N, 13.36.

EXAMPLE 12

Synthesis of Z-1-Methyl-Histidine

1-Methyl-histidine (commercially available from Sigma Chemical Co.) (507 mg, 2.58 mmol) was suspended in 50 ml methylene chloride and to this was added trimethylsilyl chloride (1.26 g, 11.61 mmol). This mixture was stirred and refluxed for 1 hour and then cooled in an ice bath. Diisopropylethyl amine (2.0 g, 15.5 mmol) was slowly added with cooling. Carbobenzoxy chloride (661 mg, 3.88 mmol) was added and the entire mixture was stirred at RT for 4 hours.

The methylene chloride was evaporated and 30 ml of $H_2O$ added. The mixture was extracted with $3\times 5$ ml $Et_2O$ and then acidified with HCl to pH 4. The aqueous layer was lyophilized to give 820 mg of a white solid. This material was purified on a Magnum 20-ODS3 reversed phase column with a linear gradient of 0–10% 1% AcOH/CH3CN—$H_2O$. The main peak was collected and lyophilized to yield a white, amorphous powder (675 mg, 86%) of Z-1-methyl-histidine.

HPLC: Homogeneous; mp 105°–7° C.; $[\alpha]_D$ −0.77° (c 0.9, DMF); 100 MHz NMR (DMSO-$d_6$): 2.85 (m, 2H), 3.57 (S, 3H), 4.35 (bs, 3H), 5.01 (S, 2H), 6.84 (S, 1H), 7.34 (S, 5H), 7.48 (S, 1H).

Anal. Cald. for $C_{15}H_{17}N_3O_4$ (303.32): C, 59.39; H, 5.65; N, 13.85. Found: C, 58.93; H, 5.59; N, 13.92.

REFERENCES

1. K. Barlos, D. Papaioannou and D. Theodoropoulos, J. Org. Chem. 47, 1324 (1982).
2. E. Smithwick, Jr. and R. Shuman, J. Org. Chem. 39, 3441 (1974).
3. C. D. Chang, M. Waki, M. Ahmad, J. Meienhofer, E. Lundell, and J. Haug, Int J. Pept. Prot. Res., 15, 59–66 (1980).

I claim:

1. A method for preparing an essentially 100% pure amino-terminus protected amino acid comprising:
   a. silylating one equivalent of a naturally occurring amino acid with at least two equivalents of a silylating agent in the presence of an organic solvent and an organic base;
   b. acylating the reaction product of step (a) with an amino terminus acylating agent to form an amino terminus protected amino acid silyl ester; and
   c. hydrolyzing the amino terminus protected amino acid silyl ester with an aqueous base whereby an essentially 100% pure amino terminus protected amino acid is formed.

2. The method of claim 1, wherein the amino acid is one selected from the group consisting of glycine, alanine, phenylalanine, valine, proline, glutamine, methionine, tryptophan, aspartic acid, leucine, isoleucine, glutamic acid, lysine, serine, asparagine, cysteine and threonine.

3. The method of claim 1, wherein the amino acids tryptophan, aspartic acid, glutamic acid, lysine, serine, cysteine, tyrosine, arginine, histidine, and threonine may be protected on the side chain functionality by a blocking group selected from the group consisting of formyl, t-butyl, t-butyloxycarbonyl, benzyl, halobenzyl, benzyloxycarbonyl, and halobenzyloxycabonyl.

4. The method of claim 1, wherein the silylating agent is trimethylsilylchloride.

5. The method of claim 1, wherein the organic solvent is methylene chloride.

6. The method of claim 1, wherein the organic base is diisopropylethylamine.

7. The method of claim 1, wherein the amino terminus acetylating agent is 9-fluorenylmethyloxycarbonyl.

8. The method of claim 7, wherein the 9-fluorenylmethyloxycabonyl is 9-fluorenylmethyloxycarbonyl chloride.

9. The method of claim 1, wherein the amino terminus acylating agent is one selected from the group consisting of benzyloxycarbonyl, 2,2,2-trichloroethyloxycarbonyl, and t-butyloxycarbonyl.

* * * * *

UNITED STATES PATENT AND TRADEMARK OFFICE
CERTIFICATE OF CORRECTION

PATENT NO. : 4,822,890
DATED : April 18, 1989
INVENTOR(S) : David R. Bolin

It is certified that error appears in the above-identified patent and that said Letters Patent is hereby corrected as shown below:

In Claim 3: in column 12 on line 32, after claim delete "1" and insert therefor -- 2 --.

Signed and Sealed this

Twenty-third Day of January, 1990

Attest:

JEFFREY M. SAMUELS

*Attesting Officer*    Acting Commissioner of Patents and Trademarks